(12) United States Patent
Ochrombel (10) Patent No.: US 9,851,385 B2
(45) Date of Patent: Dec. 26, 2017

(54) METHOD AND APPARATUS FOR DETERMINING THE PRESENCE OF AN ELECTRICAL CHARGE ON THE SURFACE OF A LENS MOLD

(71) Applicant: Novartis AG, Basel (CH)

(72) Inventor: Rene Ochrombel, Bergheim (DE)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 15/351,917

(22) Filed: Nov. 15, 2016

(65) Prior Publication Data

US 2017/0168103 A1    Jun. 15, 2017

Related U.S. Application Data

(60) Provisional application No. 62/266,071, filed on Dec. 11, 2015.

(51) Int. Cl.

| | |
|---|---|
| *G01J 4/00* | (2006.01) |
| *G01R 29/24* | (2006.01) |
| *G01N 21/21* | (2006.01) |
| *B29D 11/00* | (2006.01) |
| *G01R 1/07* | (2006.01) |
| *G01R 15/24* | (2006.01) |

(52) U.S. Cl.
CPC ........ *G01R 29/24* (2013.01); *B29D 11/00125* (2013.01); *G01N 21/21* (2013.01); *G01R 1/071* (2013.01); *G01R 15/24* (2013.01)

(58) Field of Classification Search
CPC ............................................. G01J 4/00
USPC ............................................. 356/364
See application file for complete search history.

(56) References Cited

U.S. PATENT DOCUMENTS

| 4,999,570 A | 3/1991 | Ehrler |
| 7,084,616 B1 | 8/2006 | Frank et al. |
| 7,875,217 B2* | 1/2011 | Yin ................. B29D 11/00 264/1.36 |

FOREIGN PATENT DOCUMENTS

WO      2015091585 A1    6/2015

* cited by examiner

*Primary Examiner* — Roy M Punnoose
(74) *Attorney, Agent, or Firm* — Robert A. Ambrose (57) ABSTRACT

A method for determining the presence of an electrical charge on a surface of an ophthalmic lens mold including the steps of exposing a sensor crystal of a sensor element to a surface of an ophthalmic lens mold on which an electrical charge generating an electrical field may be present, converting a light beam emitted from a laser light source into a linearly polarized measurement light beam by passing the light beam through the sensor element, processing the linearly polarized measurement light beam exiting the sensor element in a measurement unit, wherein the sensor crystal is selected from a non-centrosymmetrical crystallographic point group $\overline{4}3$ m.

20 Claims, 2 Drawing Sheets

METHOD AND APPARATUS FOR DETERMINING THE PRESENCE OF AN ELECTRICAL CHARGE ON THE SURFACE OF A LENS MOLD

This application claims the benefit under 35 U.S.C. §119(e) of U.S. provisional application Ser. No. 62/266,071 filed on Dec. 11, 2015, herein incorporated by reference in its entirety.

FIELD

The invention relates to a method and an apparatus for determining the presence of an electrical charge on the surface of a lens mold, particularly a contact lens mold, in particular a soft contact lens mold.

BACKGROUND

Contact lenses, in particular soft contact lenses for single use, are nowadays produced in large volumes in highly automated manufacturing processes and facilities. These contact lenses can be manufactured using reusable male and female mold halves which are typically made out of glass. When mated to form the mold, these mold halves define a hollow mold cavity between the lens forming surfaces of the male and the female mold half. Prior to mating the male and female mold haves to close the mold, a lens forming material is dosed into the female mold half. Examples of such lens forming materials include polymers and pre-polymers based on polyvinyl alcohols (PVA), silicone hydrogels (SiHy) or on polyethylene glycols (PEG) or other suitable lens forming materials known in the art. After closing the mold, the lens forming material contained in the mold cavity is cured through polymerization and/or cross-linking to form the contact lens.

During manufacturing of such contact lenses, it may occur, that air bubbles get entrapped in the lens forming material resulting in a contact lens which will be rejected during the lens inspection step, as the entrapped air bubbles may lead to a poor quality of the lens. It is believed that the formation of air bubbles may result from a non-uniform and/or non-symmetric wetting of the respective mold half by the lens forming material. For example, as the male mold half is moved towards, the lens forming material contained in the female mold half, in case the first contact of the lens forming surface of the male mold half does not occur at a predefined single point, a non-homogeneous wetting might result with an entrapment of air bubbles.

To overcome this problem of air bubble entrapment, an electrostatic charge is provided onto the lens forming surface on at least one of the mold halves prior to the lens forming surface coming into contact with said lens forming material. The electrostatic charge may be deposited onto the lens forming surface by a charging electrode discharging charges onto the respective lens forming surface or by a triboelectrical stamp carrying an electrical charge and contacting the lens forming surface of the mold half.

This step of applying an electrical charge to the lens forming surface has to be repeated before each lens molding process, in particular after rinsing and drying of the mold halves. For various reasons, the deposition of the electrical charge onto the lens forming surface may not occur properly so that no electrical charge is present on the lens molding surface, or the charge is deposited at a location of the lens mold other than the lens forming surface.

Therefore, a method for reliably allow for contactless detection of an electrical charge on the lens forming surface of a lens mold is needed.

SUMMARY OF THE INVENTION

To achieve these objects, the present invention suggests a method and a device as it is specified by the features of the independent claim. Advantageous aspects of the device according to the invention are the subject matter of the dependent claims.

Throughout the entire specification, whenever the term "lens mold" is used this term is to be understood to also denote only a part of an entire lens mold such as, for example, a mold half. Also, as used in the specification including the appended claims, the singular forms "a", "an", and "the" include the plural, unless the context explicitly dictates otherwise. When using the term "about" with reference to a particular numerical value or a range of values, this is to be understood in the sense that the particular numerical value referred to in connection with the "about" is included and explicitly disclosed, unless the context clearly dictates otherwise. For example, if a range of "about" numerical value a to "about" numerical value b is disclosed, this is to be understood to include and explicitly disclose a range of numerical value a to numerical value b. Also, whenever features are combined with the term "or", the term "or" is to be understood to also include "and" unless it is evident from the specification that the term "or" must be understood as being exclusive.

In one aspect, the invention suggests a method for determining the presence of an electrical charge on a surface of an ophthalmic lens mold. The method comprises the steps of
 exposing a sensor crystal of a sensor element to a surface of an ophthalmic lens mold on which an electrical charge generating an electrical field may be present,
 converting a light beam emitted from a laser light source into a linearly polarized measurement light beam by passing the light beam through the sensor element,
 processing the linearly polarized measurement light beam exiting the sensor element in a measurement unit.

The step of converting the light beam into a linearly polarized measurement light beam by passing the light beam through the sensor element comprises:
 converting the light beam emitted from the laser light source into a linearly polarized light beam having a first polarization direction by passing the light beam through a linear polarizer,
 converting the linearly polarized light beam exiting the linear polarizer into an elliptically polarized light beam by passing the linearly polarized light beam through the sensor crystal, the sensor crystal being selected from a non-centrosymmetrical crystallographic point group $\overline{4}3m$,
 converting the elliptically polarized light beam exiting the sensor crystal into the linearly polarized measurement light beam by passing the elliptically polarized light beam through a quarter-wave polarizer.

The linearly polarized measurement light beam has a second polarization direction forming a polarization angle with the first polarization direction of the linearly polarized light beam exiting the linear polarizer and entering the sensor crystal. The polarization angle of the linearly polarized measurement light beam is representative of the presence of the electrical field generated by the electrical charge on the surface of the lens mold which the sensor crystal is exposed to.

The step of processing the linearly polarized measurement light beam in the measurement unit comprises:
rotating the second polarization direction of the linearly polarized measurement light beam by passing the polarized measurement light beam through a Faraday rotator thereby forming a rotated linearly polarized measurement light beam,
converting the rotated linearly polarized measurement light beam into an analyzer light beam by passing the rotated linearly polarized measurement light beam through an analyzer,
converting the analyzer light beam into an electrical detection signal with the aid of a photodetector and evaluating the electrical detection signal generated by the photodetector with the aid of an evaluator thereby determining the presence of the electrical charge on the surface of the ophthalmic lens mold.

According to a further aspect of the method according to the invention, the propagation direction of the light beam passing through the sensor element is perpendicular to the surface of the ophthalmic lens mold the sensor crystal is exposed to.

According to a still further aspect of the method according to the invention, the sensor crystal is selected from the non-centrosymmetrical crystallographic point group $\bar{4}3m$ and has crystallographic faces along the crystallographic planes $[1\bar{1}0]\times[110]\times[001]$, wherein the electrical field is parallel to the direction of the crystallographic plane $[110]$, and wherein the propagation direction of the linearly polarized light beam exiting the linear polarizer and entering the sensor crystal has a propagation direction parallel to the crystallographic plane $[1\bar{1}0]$ Still in accordance with another aspect of the device according to the invention, the analyzer is a linear polarizer allowing light having a third polarization direction perpendicular to the first polarization direction of the linearly polarized light beam exiting the linear polarizer and entering the sensor crystal to pass through the analyzer.

In accordance with a further aspect of the method according to the invention, evaluating the electrical detection signal generated by the photodetector is performed in the evaluator using a phase-locked loop, the evaluator controlling a direct current driving the Faraday rotator to rotate the second polarization direction of the linearly polarized measurement light beam by an angle determined by the electrical detection signal generated by the photodetector and evaluated by the evaluator.

According to a further aspect of the method according to the invention, the second polarization direction of the linearly polarized measurement light beam is rotated by passing the linearly polarized measurement light beam through a first Faraday rotator thereby forming a non-modulated rotated polarized measurement light beam, and by thereafter passing the non-modulated rotated linearly polarized measurement light beam through a second Faraday rotator thereby forming a modulated rotated linearly polarized measurement light beam, with the first Faraday rotator being driven by a direct current supplied by a direct current driver controlled by the evaluator, and with the second Faraday rotator being driven by an alternating current supplied by an alternating current driver connected to an oscillator.

According to a still further aspect of the method according to the invention, the modulated rotated linearly polarized measurement light beam is converted into the electrical detection signal, and the direct current supplied by the direct current driver controlled by the evaluator and driving the first Faraday rotator is varied by the phase-locked loop of the evaluator until the modulated electrical detection signal is symmetrical around a minimum value.

Yet in accordance with another aspect of the method according to the invention, the sensor crystal is a single crystal selected from the group comprising of $Bi_4Ge_3O_{12}$, $Bi_4Si_3O_{12}$ and GaAs.

In accordance with a still further aspect of the method according to the invention, the photodetector is a PIN-diode.

Yet in accordance with another aspect of the method according to the invention, the laser light source is a helium-neon laser or a laser diode.

According to a further aspect of the method according to the invention, the surface of the lens mold is a lens forming surface.

Still in accordance with another aspect of the method according to the invention, the distance between the surface of the lens mold and the sensor crystal is in the range of 0.5 mm to 20 mm.

In another aspect, the invention suggests an apparatus for determining the presence of an electrical charge on a surface of an ophthalmic lens mold. The apparatus comprises:
a laser light source for emitting a light beam defining a beam path,
a sensor element comprising a sensor crystal arranged in the beam path of the light beam, the sensor crystal being exposable to a surface of an ophthalmic lens mold on which an electrical charge generating an electrical field may be present, the sensor element being configured for converting the light beam emitted by the laser light source into a linearly polarized measurement light beam by having the light beam emitted by the laser light source pass through the sensor element,
a measurement unit for processing the linearly polarized measurement beam exiting the sensor element.

The sensor element comprises
a linear polarizer having a first polarization direction and being arranged in the beam path of the light beam, the linear polarizer being configured for converting the linearly polarized light beam emitted from the laser light source into a polarized light beam having a first polarization direction,
the sensor crystal which is selected from the non-centrosymmetrical crystallographic point group $\bar{4}3m$, the sensor crystal being arranged in the beam path of the polarized light beam, for converting the linearly polarized light beam exiting the linear polarizer into an elliptically polarized light beam, and
a quarter-wave polarizer being arranged in the beam path of the elliptically polarized light beam exiting the sensor crystal, the quarter-wave polarizer being configured for converting the elliptically polarized light beam into the linearly polarized measurement light beam having a second polarization direction forming a polarization angle with the first polarization direction of the linearly polarized light beam exiting the linear polarizer and entering the sensor crystal, the polarization angle of the linearly polarized measurement light beam being representative of the presence of the electrical field generated by the electrical charge on the surface of the lens mold which the sensor crystal is exposable to.

The measurement unit comprises
a Faraday rotator arranged in the beam path of the linearly polarized measurement light beam and configured for rotating the second polarization direction of the linearly polarized measurement light beam to form a rotated linearly polarized measurement light beam, an analyzer being arranged in the beam path of the rotated linearly polarized measurement light beam, the analyzer being configured for converting the rotated linearly polarized measurement light beam into an analyzer light beam, a photodetector for converting the analyzer light beam into an electrical detection signal, and an evaluator for evaluating the electrical detection signal generated by the photodetector to determine the presence of the electrical charge on the surface of the ophthalmic lens mold.

According to one aspect of the apparatus according to the invention, the sensor crystal is selected from the non-centrosymmetrical crystallographic point group $\overline{4}3m$ and has crystallographic faces along the crystallographic planes $[1\overline{1}0]\times[110]\times[001]$.

According to yet another aspect of the apparatus according to the invention, the measurement unit comprises a first Faraday rotator arranged in the path of the polarized measurement light beam and connected to a direct current driver controlled by the evaluator, for rotating the second polarization direction of the linearly polarized measurement light beam to form a non-modulated rotated linearly polarized measurement light beam, and a second Faraday rotator arranged in the path of the non-modulated rotated linearly polarized measurement light beam and connected to an alternating current driver to form a modulated rotated linearly polarized measurement light beam.

The analyzer of the measurement unit is a linear polarizer having a polarization direction perpendicular to the polarization direction of the linear polarizer of the sensor element.

Due to the simple set-up of the method according to the invention and the use of at least one Faraday rotator, no mechanical parts are needed for evaluating the electrical field the sensor element is exposed to, while at the same time the method provides for a very reliable measurement of the presence of an electrical field generated by an electrical charge which may be present on the surface of the ophthalmic lens mold. As no mechanical parts are used, a mechanical failure may not occur during the process of determining whether or not there is an electrical charge present on the surface of the ophthalmic lens mold. Furthermore, even a small quantity of an electrical charge can be detected. In sum, the method is substantially temperature independent, has a high sensitivity while being capable of detecting the presence of an electrical charge without contacting the surface carrying the electrical charge.

In the sensor crystal selected from the non-centrosymmetrical crystallographic point group $\overline{4}3m$, induced linear birefringence only occurs when the sensor crystal is exposed to an electrical field.

The use of a sensor crystal selected from the point group $\overline{4}3m$ additionally improves the measurement as crystals selected from the $\overline{4}3m$ point group generally do not display any optical activity.

The quarter-wave polarizer is particularly a Sénarmont compensator whose main axes of the indicatrix will particularly be parallel and perpendicular, respectively, to the polarization direction of the linear polarizer 21 of the sensor element 2

The propagation direction parallel to the crystallographic plane $[1\overline{1}0]$ provides for an increased quality of the detection as the polarization direction of the linearly polarized light beam enters the sensor crystal with an angle of 45° with respect to the main axes of the sensor crystal, thereby ensuring that both directions of oscillation, the one parallel to $\lfloor 11-\sqrt{2} \rfloor$ and the one parallel to $\lfloor 11\sqrt{2} \rfloor$, are stimulated with the same amplitude within the sensor crystal for optimal optical retardation of the two partial waves so formed.

When using an analyzer in the measurement unit in form of a polarizer allowing only light to pass through the analyzer having a third polarization direction which is perpendicular to the first polarization direction of the linearly polarized light beam generated by the linear polarizer of the sensor element, the detection signal generated by the photodetector decreases to a minimum once the rotated polarized measurement light beam generated by the Faraday rotator is such that the polarization direction of the rotated polarized measurement light beam corresponds to the polarization direction of the light beam entering the sensor crystal. In this case, the Faraday rotator has fully compensated the polarization angle that has been caused by the sensor crystal which is exposed to the electrical field generated by the electrical charge on the surface of the ophthalmic lens mold.

The phase-locked loop in the evaluator allows for a very precise, simple and automated evaluation of the polarization angle by generating a signal depending on the detection signal generated by the photodetector that causes the current driver connected to the Faraday rotator to be adjusted until the second polarization angle of the linearly polarized measurement light beam is fully compensated. While other phase-locked loops may be used, a phase-locked loop comprising a lock-in amplifier is particularly effective for the evaluation of the second polarization angle of the linearly polarized measurement light beam caused by the sensor crystal (and the quarter-wave polarizer arranged downstream of the sensor crystal in the sensor element) when being exposed to the electrical field generated by the electrical charge on the surface of the ophthalmic lens mold.

The use of a first Faraday rotator driven by a direct current and of a second Faraday rotator driven by an alternating current allows for a very simple and efficient evaluation of the polarization angle with the aid of the phase-locked loop in the evaluator.

In particular, the phase-locked loop uses the frequency of the modulation of the polarization direction of the rotated polarized measurement light beam which is contained in the electrical detection signal generated by the photodetector, this modulation of the polarization direction being generated by the second Faraday rotator driven by the alternating current. The phase-locked loop determines the amplitude of the direct current that must be supplied to the first Faraday rotator at which amplitude of the direct current the second polarization angle of the linearly polarized measurement light beam caused by the sensor crystal (and the quarter-wave polarizer arranged downstream of the sensor crystal in the sensor element) is rotated back to the first polarization direction of the linearly polarized light beam entering the sensor crystal. In other words, the phase-locked loop determines the amplitude of the direct current to be supplied to the first Faraday rotator at which the rotation of the second polarization direction of the linearly polarized measurement light beam caused by the electrical field to which the sensor crystal is exposed is fully compensated. This amplitude of the direct current is representative of the strength of the electrical field generated by the electrical charge on the surface of the ophthalmic lens mold, and hence is representative of the quantity of the electrical charge present on the surface of the ophthalmic lens mold.

The phase-locked loop in the evaluator driving a first and a second Faraday rotator allows for very precise evaluation of the polarization angle within a range of ±0.001° rotation angle and therefore allows the measurement even of very weak electrical fields generated by small quantities of an electrical charge on the surface of the ophthalmic lens mold. By way of example, the method for measurement according to the present invention allows the detection of electrical fields as weak as about 1 V/cm (Volts per centimeter). The method according to the present invention is therefore particularly suited for the detection and measurement of an electrical charge on the surface of an ophthalmic lens mold.

BRIEF DESCRIPTION OF THE DRAWINGS

Embodiments of the method and apparatus according to the invention are described in more detail with reference to the accompanying drawings, in which.

DETAILED DESCRIPTION OF EMBODIMENTS

Figure 1:
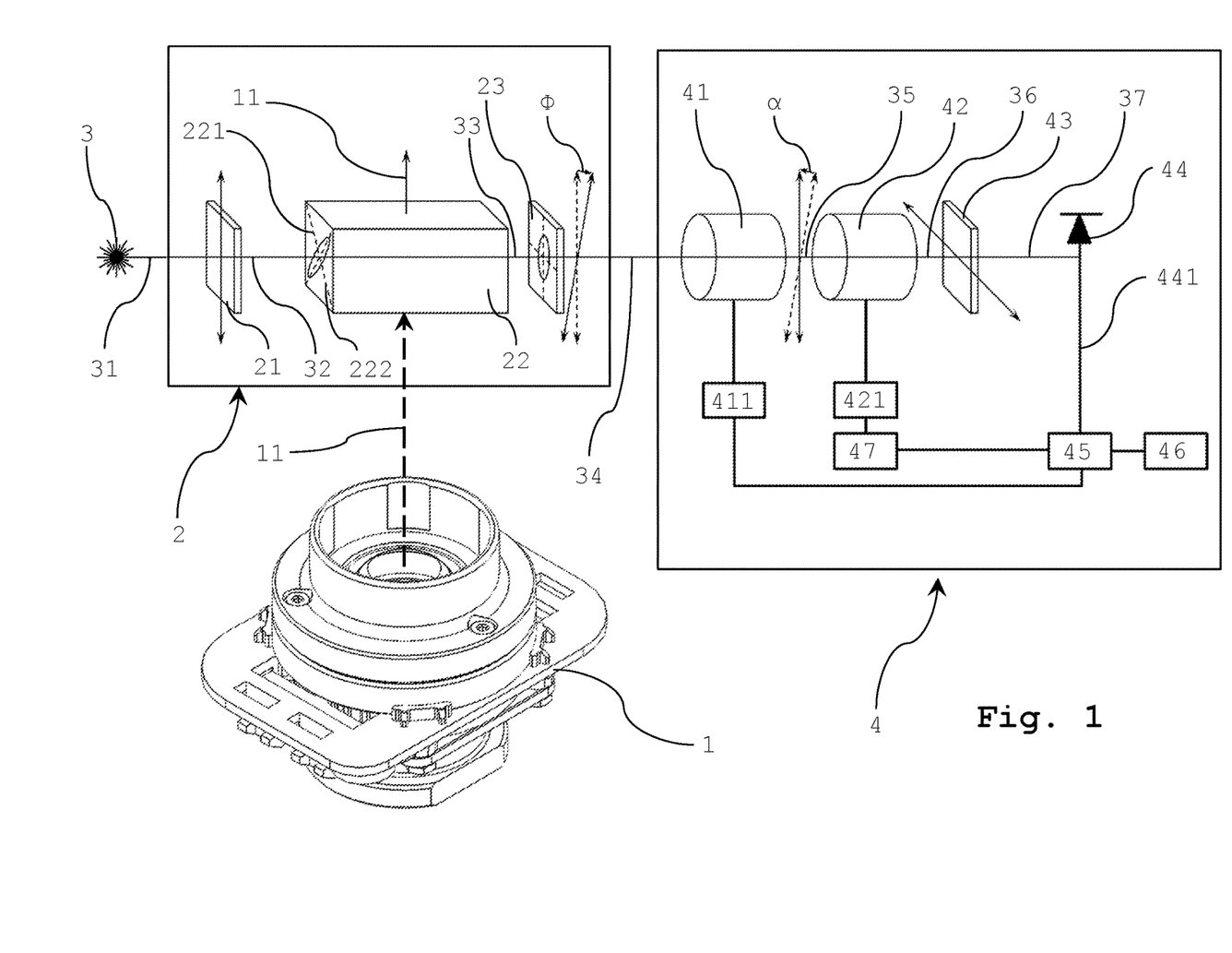
FIG. 1 shows a set-up of components of an embodiment of an apparatus according to the invention for performing the method for determining the presence of an electrical charge on the surface of a male contact lens mold, FIG. 2 schematically shows the arrangement of a sensor crystal arranged above a female contact lens mold, and FIG. 3 schematically shows the sensor crystal arranged above the male contact lens mold already shown in FIG. 1.

FIG. 1 shows a set-up of components of an embodiment of an apparatus according to the invention for performing the method according to the invention. The set-up comprises a helium-neon laser 3 as laser light source for emitting a light beam 31 which is passed through a sensor element 2. The sensor element 2 comprises a linear polarizer 21, a sensor crystal 22 selected from the non-centrosymmetrical crystallographic cubic point group $\bar{4}3m$ and exhibiting an electro-optical behavior when exposed to an electrical field 11, and a quarter-wave polarizer 23. For example, the quarter-wave polarizer is a Sénarmont compensator whose main axes of the indicatrix will be parallel and perpendicular, respectively, to the polarization direction of the linear polarizer 21 of the sensor element 2. The sensor crystal 22 is, for example, a single crystal of $Bi_4Ge_3O_{12}$ which has crystallographic faces along the crystallographic planes $[1\bar{1}0] \times [110] \times [001]$.

The set-up of components of the apparatus further includes a measurement unit 4 comprising a first Faraday rotator 41 and a second Faraday rotator 42, an analyzer 43, and a photodetector 44 connected to an evaluator 45. The set-up further comprises an oscillator 47 which is connected to the second Faraday rotator 42 through an alternating current driver 421, and which is further connected to the evaluator 45. The evaluator 45 is additionally connected on one hand to the first Faraday rotator 41 through a direct current driver 411, and on the other hand to a display unit 46.

Each of the Faraday rotators 41, 42 may comprise a cell filled with water and surrounded by a coil through which a current may flow. The analyzer 43 may comprise a linear polarizer having a polarization direction which is perpendicular to the polarization direction of the linear polarizer 21 of the sensor element 2. The photodetector 44 may comprise a PIN-diode (Positive-Intrinsic-Negative). The evaluator 45 may comprises a lock-in amplifier (not shown in detail).

Figure 2:
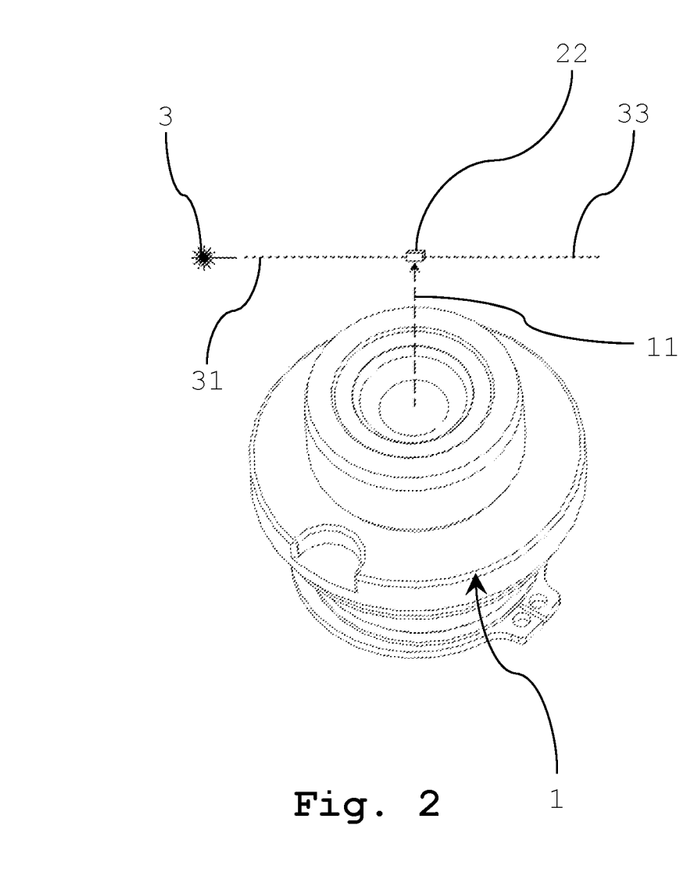
Figure 3:
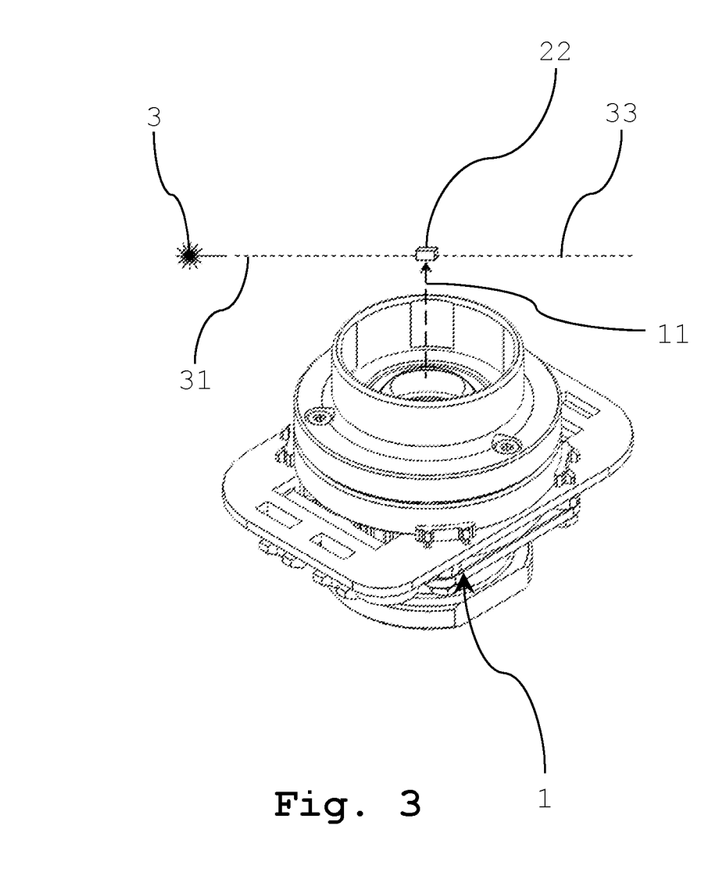

FIG. 2 schematically shows the sensor crystal 22 arranged above a female contact lens mold 10, and FIG. 3 schematically shows the sensor crystal 22 arranged above the male contact lens mold 1 already shown in FIG. 1.

Operation of the apparatus and the method for determining the presence of an electrical charge on a surface of a male contact lens mold 1 is described in the following with reference to FIG. 1.

The light beam 31 emitted from the helium-neon laser 3 passes through the linear polarizer 21 to form a linearly polarized light beam 32 having a first polarization direction which is determined by the linear polarizer 21. The resulting linearly polarized light beam 32 then passes through the sensor crystal 22. Due to the specific crystalline parameters of the sensor crystal 22 and due to the electrical field 11 to which the sensor crystal 22 is exposed and which is caused by an electrical charge on the surface of the male contact lens mold 1, the linearly polarized light beam 32 is converted into an elliptically polarized light beam 33. The elliptically polarized light beam 33 exiting the sensor crystal 22 then passes through the quarter-wave polarizer 23 (e.g. Sénarmont compensator). The quarter-wave polarizer 23 converts the elliptically polarized light beam 33 back into a linearly polarized measurement light beam 34. This linearly polarized measurement light beam 34 has a second polarization direction which is different from the first polarization direction of the linearly polarized light beam 32 entering the sensor crystal 22 and includes a polarization angle φ with the first polarization direction.

The linearly polarized measurement light beam 34 exiting the sensor element 2 and having the second polarization direction then enters the measurement unit 4, and in particular it enters the first Faraday rotator 41. The first Faraday rotator 41 is driven by a direct current supplied by the direct current driver 411 so to rotate back the second polarization direction of the linearly polarized measurement light beam 34 by an angle α, thereby forming a non-modulated rotated linearly polarized measurement light beam 35. Accordingly, the polarization direction of the non-modulated rotated linearly polarized measurement light beam 35 includes an angle φ-α with the first polarization direction of the linearly polarized light beam 32 entering the sensor crystal. The non-modulated rotated linearly polarized measurement light beam 35 then enters the second Faraday rotator 42 which is driven by an alternating current supplied by the alternating current driver 421 having a frequency generated by the oscillator 47. The second Faraday rotator modulates the polarization direction of the non-modulated rotated linearly polarized measurement light beam 35 about a central polarization direction which is the polarization direction including the angle φ-α with the first polarization direction of the linearly polarized light beam 32, thereby forming a modulated rotated linearly polarized measurement light beam 36.

The modulated rotated linearly polarized measurement light beam 36 then impinges on the analyzer 43 (a linear polarizer) which has a polarization direction which is perpendicular to the first polarization direction of the linearly polarized light beam 32 entering the sensor crystal 22, so that the analyzer 43 only allows light having a polarization direction which is perpendicular to the first polarization direction of the linearly polarized light beam 32 to pass through the analyzer 43. The so formed analyzer light beam 37 exiting the analyzer 43 then impinges on PIN-diode 44 which converts the analyzer light beam 37 into the electrical detection signal 441. The electrical detection signal 441 generated by PIN-diode 44 is then forwarded to the evaluator 45. The evaluator 45 evaluates the electrical detection signal 441 generated by the PIN-diode 44.

The aim now is to compensate the angle φ which is caused by the electrical field generated by the electrical charge on the surface of the male contact lens mold 1, to which electrical field the sensor crystal 22 is exposed (assuming that there is an electrical charge present on the surface of the male contact lens mold 1). Or to say it in other words, the aim is to rotate the second polarization direction of the linearly polarized measurement light beam 34 back by an angle α that fully compensates the angle φ.

In this case, the polarization direction of the non-modulated rotated linearly polarized measurement light beam 35 is identical with the first polarization direction of the linearly polarized light beam 32, and this polarization direction of the non-modulated rotated linearly polarized measurement light beam 35 is perpendicular to the polarization direction of the analyzer 43. Accordingly—and further assuming that there would be no modulation of the non-modulated rotated linearly polarized measurement light beam 35 and the analyzer is a perfect linear polarizer—there would be no analyzer light beam 37, and the electrical signal generated by the PIN-diode 44 would consequently be zero.

However, in fact it is the modulated rotated linearly polarized measurement light beam 36 that impinges on the analyzer 43. In addition, as polarizers—here the analyzer 43—generally do not perfectly block the light polarized in a direction perpendicular to their polarization axis, the electrical detection signal 441 generated by the PIN-diode 44 can only decrease to a minimum, even if no modulation were present. At this minimum the electrical detection signal 441 is symmetrically modulated about that minimum, as it is the modulated rotated linearly polarized measurement light beam 36 that impinges on the analyzer 43, so that the analyzer light beam 37 impinging on the PIN-diode 44 contains modulation and, consequently, also the electrical detection signal 441 contains modulation.

As long as the polarization direction of the non-modulated rotated linearly polarized measurement light beam 35 has a polarization direction that deviates from the polarization direction of the linearly polarized light beam 32 entering the sensor crystal 22 (or to say it in other words, as long as the angle φ has not been fully compensated by the first Faraday rotator 41), the electrical detection signal 441 generated by the PIN-diode (containing the modulation) is not symmetrical. This non-symmetry is detected by the evaluator 45 and means that the direct current supplied to the first Faraday rotator 41 by the direct current driver 411 is not the proper direct current needed to fully compensate the angle φ. The evaluator 45 then generates a signal that causes the direct current driver 441 to adjust the direct current supplied to the first Faraday rotator 41 until the above-described symmetry of the electrical signal 441 generated by the PIN-diode 44 is reached.

In general, the minimum of the electrical signal 441 generated by the PIN-diode 44 (i.e. the direct current necessary to fully compensate the angle φ) can also be detected without modulating the non-modulated rotated linearly polarized measurement light beam 35, so that generally the second Faraday rotator 42 is only optional. However, modulating the non-modulated rotated linearly polarized measurement light beam 35 is advantageous as it is easier to detect the minimum of the electrical signal 441 by means of the afore-mentioned symmetry of the electrical signal about that minimum, as is explained in the following.

The polarization of the non-modulated rotated linearly polarized measurement light beam 35 exiting the first Faraday rotator 41 is modulated by the alternating magnetic field of the second Faraday rotator 42 which is supplied with an alternating current generated by the alternating current driver 421 and having a frequency determined by the oscillator 47. This frequency determined by the oscillator is also used as reference frequency for the lock-in amplifier of the evaluator 45 receiving the electrical signal 441 generated by the PIN-diode 44. The electrical signal 441 generated by the PIN diode 44 contains an alternating component having the frequency of the modulation, i.e. the frequency determined by the oscillator 47. However, the alternating component contained in the electrical signal 441 is only symmetrical in case the electrical signal 441 is modulated about the minimum (i.e. only in case the direct current supplied by the direct current driver 411 to the first Faraday rotator 41 is such that the angle φ is fully compensated by the first Faraday rotator 41). In case the angle φ is not fully compensated by the first Faraday rotator 41, the electrical signal 441 generated by the PIN-diode 44 is not symmetrical. Whether or not this electrical signal 441 is symmetrical can be easily detected by the lock-in amplifier, as the evaluator 45 is connected to the oscillator 47 so that the frequency of the oscillator is also available for the lock-in amplifier.

Once the symmetry of the electrical signal 441 has been detected by the lock-in amplifier of the evaluator 45, the direct current supplied to the first Faraday rotator 41 by the direct current driver 411 is the proper direct current needed to rotate the polarization direction of the linearly polarized measurement light beam 34 back by an angle α that exactly corresponds to the angle φ caused by the electrical field to which the sensor crystal 22 is exposed (this electrical field being generated by the electrical charge on the surface of the male contact lens mold 1). From this direct current the strength of the electrical field (generated by the electrical charge on the surface of the male contact lens mold) can be determined.

The lock-in amplifier of the evaluator 45 allows for very precise evaluation of the polarization angle φ within 0.001° rotation and therefore allows for the measurement of very weak electrical fields 11 generated by small quantities of electrical charges on the surface of the contact lens mold 1. Hence, the method for measurement according to the present invention allows for detecting electrical fields 11 in the range of 1 V/cm.

In the following it is explained in more detail how the linearly polarized light beam 32 entering the sensor crystal 22 is converted into the elliptically polarized light beam exiting the sensor crystal 22. The sensor crystal 22 (e.g. single crystal of $Bi_4Ge_3O_{12}$) is selected such that it displays a linear electro-optic birefringence occurring in crystals that lack inversion symmetry, such as non-centrosymmetric crystals. The birefringence is induced in the sensor crystal 22 by an electrical field 11 caused by the electrical charge on the surface of the male contact lens mold 1 to which the sensor crystal 22 is exposed.

The birefringence is proportional to the electrical field 11 the sensor crystal 22 is exposed to. In the absence of any electrical field 11, the linearly polarized light beam 32 is not affected by the cubic sensor crystal 22 belonging to the crystallographic cubic point group $\bar{4}3m$. In case the sensor crystal 22 is exposed to the electrical field 11, however, the linearly polarized light beam 32 entering the sensor crystal 22 is converted into an elliptically polarized light beam 33, as has been mentioned above already.

The strength of the electrical field 11 has a linear influence on the conversion of the linearly polarized light beam 32 into the elliptically polarized light beam 33 and determines the second polarization direction of the linearly polarized measurement light beam 34 after the quarter-wave polarizer 23

(e.g. Sénarmont compensator) has converted the elliptically polarized light beam 33 into the linearly polarized measurement light beam 34. Accordingly, the second polarization direction of the linearly polarized measurement light beam 34 forms a polarization angle φ which is representative of the strength of the electrical field 11 generated by the electrical charge on the surface of the lens mold 1 which the sensor crystal 22 is exposed to as will become apparent from the following description.

The sensor crystal 22 has crystallographic faces along the crystallographic planes [1$\bar{1}$0]×[110]×[001], and the electrical field 11 is parallel to the direction of the crystallographic plane [110]. The propagation direction of the linearly polarized light beam 32 having passed through the linear polarizer 21 and entering the sensor crystal 22 has a propagation direction parallel to the crystallographic plane [1$\bar{1}$0]. The specific orientation of the sensor crystal 22 with respect to the first polarization direction of the linearly polarized light beam 32 results in an arrangement in which the first polarization direction forms an angle of 45° with the electro-optical active axes 221 and 222 the sensor crystal 22 generates when being exposed to the electrical field 11.

This arrangement of the sensor crystal 2 results in the use of the transverse electro-optical Pockels effect in which the light propagation direction of the linearly polarized light beam 32 and the direction of the electrical field 11 are perpendicular to one another. In the absence of an electrical field 11, the sensor crystal 22 does not affect the linearly polarized light beam 32. However, once the sensor crystal 22 is exposed to an electrical field 11 the indicatrix of the sensor crystal 22 changes from a sphere to a rotation ellipsoid along the optical axes 221 and 222.

The propagation vector of the linearly polarized light beam 32 which is parallel to the crystallographic plane ⌊1$\bar{1}$0⌋ ensures an increased quality of the measurement as the polarization direction of the linearly polarized light beam enters the crystal with an angle of 45° with respect to the main axes of the crystal, thereby ensuring that oscillation in both oscillation directions, i.e. the directions parallel to ⌊11−$\sqrt{2}$⌋ and to ⌊11$\sqrt{2}$⌋, are stimulated with the same amplitude within the crystal for optimal optical retardation of the two partial waves formed.

The stimulation of the direction of oscillation parallel to ⌊11−$\sqrt{2}$⌋ and ⌊11$\sqrt{2}$⌋ results in an optical path difference ΔS between the two partial waves due to the different phase velocities for the two directions of oscillation induced by the electrical field 11. The optical path difference ΔS through the selected sensor crystal 22 is linearly correlated with the electrical field 11 according to equation (1).

$$\Delta S = L n^3 r_{123} |E| \text{sign} E \quad (1)$$

wherein
L is the path length of the light beam through the sensor crystal 22 (length of transmission),
n is the refractive index of the sensor crystal 22 with no electrical field 11 applied,
$r_{123}$ is the corresponding tensor element of the electro-optical tensor of the sensor crystal 22,
E is the strength of the electrical field 11 in the sensor crystal 22.

The elliptically polarized light beam 33 having passed through the sensor crystal 22 is then guided through the quarter-wave polarizer 23 (e.g. Sénarmont compensator). The quarter-wave polarizer 23 converts the elliptically polarized light beam 33 exiting the sensor crystal 22 into the linearly polarized measurement light beam 34. The optical path difference ΔS induced by the sensor crystal 22 results in the angle shift φ of the linearly polarized measurement light beam 34 with respect to the direction of the linearly polarized light beam 32 which enters the sensor crystal 22, the angle shift φ (or polarization angle) being proportional to the applied electrical field 11.

The resulting angle of polarization φ of the second polarization direction of the linearly polarized measurement light beam 34 having passed through the quarter-wave polarizer 23 (e.g. Sénarmont compensator) is linearly dependent on the optical path difference induced on the linearly polarized light beam 32 by the sensor crystal 22 exposed to the electrical field 11 relative to the first polarization direction of the linearly polarized light beam 32 entering the sensor crystal 22 according to equation (2).

$$\Delta S = \frac{\lambda}{\pi} \Phi \quad (2)$$

wherein λ is the wavelength of the light beam passing through the sensor crystal 22.

The linearly polarized measurement light beam 34 has a second polarization direction induced by the electrical field 11 and forming a polarization angle φ with the first polarization direction of the linearly polarized light beam 32 entering the sensor crystal 22. The polarization angle φ of the linearly polarized measurement light beam 34 is therefore representative of the strength of the electrical field 11 caused by the electrical charge on the surface of the contact lens mold to which the sensor crystal 22 is exposed.

The linearly polarized measurement light beam 34 has one polarization in ferromagnetic resonance with the water contained in the cell of the Faraday rotator. Applying a magnetic field to the water causes the phase velocity of the polarization which is in ferromagnetic resonance with the water to be higher than the phase velocity of the other resonance. Hence, the plane of linearly polarized light is rotated when a magnetic field is applied parallel to the propagation direction. The rotation angle α of a polarized light beam passing the Faraday rotator 41, 42 will depend on the path length of the light beam through the liquid exposed to the magnetic field in the cell, the Verdet Constant of the liquid and the magnetic field applied to the cell. The path length and the liquid generally do not change in the measurement set-up and therefore, by keeping the corresponding coefficients constant, the rotation angle α is determined by equation (3):

$$\alpha = K I B \quad (3)$$

wherein
α is the angle of rotation (in radians),
K is the Verdet Constant of the liquid ($H_2O$ at a wavelength λ of 589 nm: 3.8 rad $T^{-1}$ $m^{-1}$)
I is the length of the path (in meters) of the light beam through the liquid in the cell interacting with the magnetic field, and
B is the magnetic flux density (in tesla) in the direction of propagation of the light beam and generated by the coil surrounding the liquid-filled cell.

The Verdet Constant K is an empirical proportionality constant which varies with wavelength and temperature and is tabulated for various materials and is known in the art.

The magnetic field generated by the coils of the Faraday rotators 41, 42 is linearly related to the current flowing through the coils, and the angle by which the second polarization direction of the linearly polarized measurement light beam 34 is rotated in the Faraday rotators 41, 42 is consequently also linearly related to current passing through the respective coil.

Hence, the angle by which the second polarization direction of the linearly polarized measurement light beam 34 is rotated in the Faraday rotators 41, 42 is linearly related to the magnetic flux density of the magnetic field generated by the coil of the respective Faraday rotator 41, 42.

The invention has been described with a reference to the particular embodiments shown in FIGS. 1 to 3. However, for the skilled person it is evident that many changes and modifications can be made without departing from the general concept underlying the invention. Therefore, the scope of protection is not intended to be limited to certain embodiments but rather is defined by the appended claims.

The invention claimed is:

1. A method for determining the presence of an electrical charge on a surface of an ophthalmic lens mold (1, 10), the method comprising the steps of
exposing a sensor crystal (22) of a sensor element (2) to a surface of an ophthalmic lens mold (1) on which an electrical charge generating an electrical field may be present,
converting a light beam (31) emitted from a laser light source (3) into a linearly polarized measurement light beam (34) by passing the light beam (31) through the sensor element (2),
processing the linearly polarized measurement light beam (34) exiting the sensor element (2) in a measurement unit (4),
wherein the step of converting the light beam (31) into a linearly polarized measurement light beam (34) by passing the light beam (31) through the sensor element (2) comprises:
converting the light beam (31) emitted from the laser light source (3) into a linearly polarized light beam (32) having a first polarization direction by passing the light beam (31) through a linear polarizer (21),
converting the linearly polarized light beam (32) exiting the linear polarizer (21) into an elliptically polarized light beam (33) by passing the linearly polarized light beam (32) through the sensor crystal (22), the sensor crystal being selected from a non-centrosymmetrical crystallographic point group $\bar{4}3$ m,
converting the elliptically polarized light beam (33) exiting the sensor crystal (22) into the linearly polarized measurement light beam (34) by passing the elliptically polarized light beam (33) through a quarter-wave polarizer (23), wherein the linearly polarized measurement light beam (34) has a second polarization direction forming a polarization angle ($\phi$) with the first polarization direction of the linearly polarized light beam (32) exiting the linear polarizer (21) and entering the sensor crystal (22), the polarization angle ($\phi$) of the linearly polarized measurement light beam (34) being representative of the presence of the electrical field generated by the electrical charge on the surface of the lens mold (1) which the sensor crystal (22) is exposed to, and
wherein the step of processing the linearly polarized measurement light beam (34) in the measurement unit (4) comprises:
rotating the second polarization direction of the linearly polarized measurement light beam (34) by passing the polarized measurement light beam (34) through a Faraday rotator (41, 42) thereby forming a rotated linearly polarized measurement light beam (35, 36),
converting the rotated linearly polarized measurement light beam (35, 36) into an analyzer light beam (37) by passing the rotated linearly polarized measurement light beam (35, 36) through an analyzer (43),
converting the analyzer light beam (37) into an electrical detection signal (441) with the aid of a photodetector (44) and evaluating the electrical detection signal (441) generated by the photodetector (44) with the aid of an evaluator (45) thereby determining the presence of the electrical charge on the surface of the ophthalmic lens mold (1).

2. The method according to claim 1, wherein the propagation direction of the light beam (31) passing through the sensor element (2) is perpendicular to the surface of the ophthalmic lens mold (1) the sensor crystal (22) is exposed to.

3. The method according to claim 1, wherein the sensor crystal (22) is selected from the non-centrosymmetrical crystallographic point group $\bar{4}3$ m and has crystallographic faces along the crystallographic planes [$1\bar{1}0$]×[110]×[001], wherein the electrical field (11) is parallel to the direction of the crystallographic plane [110], and wherein the propagation direction of the linearly polarized light beam (32) exiting the linear polarizer (21) and entering the sensor crystal (22) has a propagation direction parallel to the crystallographic plane [$1\bar{1}0$].

4. The method according to claim 2, wherein the sensor crystal (22) is selected from the non-centrosymmetrical crystallographic point group $\bar{4}3$ m and has crystallographic faces along the crystallographic planes [$1\bar{1}0$]×[110]×[001], wherein the electrical field (11) is parallel to the direction of the crystallographic plane [110], and wherein the propagation direction of the linearly polarized light beam (32) exiting the linear polarizer (21) and entering the sensor crystal (22) has a propagation direction parallel to the crystallographic plane [$1\bar{1}0$].

5. The method according to claim 1, wherein the analyzer (43) is a linear polarizer allowing light having a third polarization direction perpendicular to the first polarization direction of the linearly polarized light beam (32) exiting the linear polarizer (21) and entering the sensor crystal (22) to pass through the analyzer (43).

6. The method according to claim 2, wherein the analyzer (43) is a linear polarizer allowing light having a third polarization direction perpendicular to the first polarization direction of the linearly polarized light beam (32) exiting the linear polarizer (21) and entering the sensor crystal (22) to pass through the analyzer (43).

7. The method according to claim 1, wherein evaluating the electrical detection signal (441) generated by the photodetector (44) is performed in the evaluator (45) using a phase-locked loop, the evaluator (45) controlling a direct current driving the Faraday rotator (41) to rotate the second polarization direction of the linearly polarized measurement light beam (34) by an angle ($\alpha$) determined by the electrical detection signal (441) generated by the photodetector (44) and evaluated in the evaluator (45).

8. The method according to claim 1, wherein the second polarization direction of the linearly polarized measurement light beam (34) is rotated by passing the linearly polarized measurement light beam (34) through a first Faraday rotator (41) thereby forming a non-modulated rotated linearly polarized measurement light beam (35), and by thereafter passing the non-modulated rotated linearly polarized measurement light beam (35) through a second Faraday rotator (42) thereby forming a modulated rotated linearly polarized measurement light beam (36), with the first Faraday rotator (41) being driven by a direct current supplied by a direct current driver (411) controlled by the evaluator (45), and with the second Faraday rotator (42) being driven by an alternating current supplied by an alternating current driver (421) connected to an oscillator (47).

9. The method according to claim 7, wherein the modulated rotated linearly polarized measurement light beam (36) is converted into the electrical detection signal (441), and wherein the direct current supplied by the direct current driver (411) controlled by the evaluator (45) and driving the first Faraday rotator (41) is varied by the phase-locked loop of the evaluator (45) until the modulated electrical detection signal (441) is symmetrical around a minimum value.

10. The method according to claim 8, wherein the modulated rotated linearly polarized measurement light beam (36) is converted into the electrical detection signal (441), and wherein the direct current supplied by the direct current driver (411) controlled by the evaluator (45) and driving the first Faraday rotator (41) is varied by the phase-locked loop of the evaluator (45) until the modulated electrical detection signal (441) is symmetrical around a minimum value.

11. The method according to claim 1, wherein the sensor crystal (22) is a single crystal selected from the group consisting of $Bi_4Ge_3O_{12}$, $Bi_4Si_3O_{12}$ and GaAs.

12. The method according to claim 1, wherein the photodetector (44) is a PIN-diode.

13. The method according to claim 2, wherein the photodetector (44) is a PIN-diode.

14. The method according to claim 1, wherein the laser light source (3) is a helium-neon laser or a laser diode.

15. The method according to claim 1, wherein the surface of the lens mold (1) is a lens forming surface.

16. The method according to claim 1, wherein the distance between the surface of the lens mold (1) and the sensor crystal (22) is in the range of 0.5 mm to 20 mm.

17. The method according to claim 2, wherein the distance between the surface of the lens mold (1) and the sensor crystal (22) is in the range of 0.5 mm to 20 mm.

18. An apparatus for determining the presence of an electrical charge on a surface of an ophthalmic lens mold (1) comprising:
a laser light source (3) for emitting a light beam (31) defining a beam path,
a sensor element (2) comprising a sensor crystal (22) arranged in the beam path of the light beam (31), the sensor crystal (22) being exposable to a surface of an ophthalmic lens mold on which an electrical charge generating an electrical field (11) may be present, the sensor element (2) being configured for converting the light beam (31) emitted by the laser light source (3) into a linearly polarized measurement light beam (34) by having the light beam (31) emitted by the laser light source (3) pass through the sensor element (2),
a measurement unit (4) for processing the linearly polarized measurement beam (34) exiting the sensor element (2),
wherein the sensor element (2) comprises
a linear polarizer (21) having a first polarization direction and being arranged in the beam path of the light beam (31), the linear polarizer (21) being configured for converting the light beam (31) emitted from the laser light source (3) into a linearly polarized light beam (32) having a first polarization direction,
the sensor crystal (22) which is selected from the non-centrosymmetrical crystallographic point group $\bar{4}3m$, the sensor crystal (22) being arranged in the beam path of the linearly polarized light beam (32) for converting the linearly polarized light beam (32) exiting the linear polarizer (21) into an elliptically polarized light beam (33), and
a quarter-wave polarizer (23) being arranged in the beam path of the elliptically polarized light beam (33) exiting the sensor crystal (22), the quarter-wave polarizer (23) being configured for converting the elliptically polarized light beam (33) into the linearly polarized measurement light beam (34) having a second polarization direction forming a polarization angle ($\phi$) with the first polarization direction of the linearly polarized light beam (32) exiting the linear polarizer (21) and entering the sensor crystal (22), the polarization angle ($\phi$) of the linearly polarized measurement light beam (34) being representative of the presence of the electrical field generated by the electrical charge on the surface of the lens mold (1) which the sensor crystal (22) is exposable to,
and wherein the measurement unit (4) comprises
a Faraday rotator (41, 42) arranged in the beam path of the linearly polarized measurement light beam (34) and configured for rotating the second polarization direction of the linearly polarized measurement light beam (34) to form a rotated linearly polarized measurement light beam (35, 36)
an analyzer (43) being arranged in the beam path of the rotated linearly polarized measurement light beam (35), the analyzer being configured for converting the rotated linearly polarized measurement light beam (35, 36) into an analyzer light beam (37),
a photodetector (44) for converting the analyzer light beam (37) into an electrical detection signal (440, 441), and
an evaluator (45) for evaluating the electrical detection signal (440, 441) generated by the photodetector (44) to determine the presence of the electrical charge on the surface of the ophthalmic lens mold (1).

19. The apparatus according to claim 18, wherein the sensor crystal (22) is selected from the non-centrosymmetrical crystallographic point group $\bar{4}3m$ and has crystallographic faces along the crystallographic planes [1$\bar{1}$0]×[110]×[001].

20. The apparatus according to claim 18, wherein the measurement unit (4) comprises
a first Faraday rotator (41) arranged in the beam path of the polarized measurement light beam (34) and connected to a direct current driver (411) controlled by the evaluator (45), for rotating the polarization direction of the linearly polarized measurement light beam (34) to form a non-modulated rotated polarized measurement light beam (35), and
a second Faraday rotator (42) arranged in the beam path of the non-modulated rotated linearly polarized measurement light beam (35) and connected to an alternating current driver (421) connected to an oscillator (47) to form a modulated rotated linearly polarized measurement light beam (36),
and wherein the analyzer (43) of the measurement unit (4) is a linear polarizer having a polarization direction perpendicular to the polarization direction of the linear polarizer (21) of the sensor element (2).

* * * * *